(12) United States Patent
Chiu et al.

(10) Patent No.: US 8,496,956 B2
(45) Date of Patent: Jul. 30, 2013

(54) IMPLANTABLE NERVE REGENERATION CONDUIT

(75) Inventors: Ing-Ming Chiu, Miaoli (TW); Shan-hui Hsu, Taichung (TW)

(73) Assignee: National Health Research Institutes, Miaoli County (TW)

( * ) Notice: Subject to any disclaimer, the term of this patent is extended or adjusted under 35 U.S.C. 154(b) by 842 days.

(21) Appl. No.: 12/492,058

(22) Filed: Jun. 25, 2009

(65) Prior Publication Data
US 2010/0068240 A1  Mar. 18, 2010

Related U.S. Application Data

(60) Provisional application No. 61/098,158, filed on Sep. 18, 2008.

(51) Int. Cl.
*A61F 13/00* (2006.01)
*A61F 2/00* (2006.01)

(52) U.S. Cl.
USPC ............. 424/426; 424/422; 424/423

(58) Field of Classification Search
None
See application file for complete search history.

(56) References Cited

U.S. PATENT DOCUMENTS

| 5,268,229 | A | * | 12/1993 | Phillips et al. | 428/400 |
| 5,496,627 | A | * | 3/1996 | Bagrodia et al. | 442/337 |
| 5,972,505 | A | * | 10/1999 | Phillips et al. | 428/397 |
| 6,858,222 | B2 | * | 2/2005 | Nelson et al. | 424/426 |

FOREIGN PATENT DOCUMENTS
WO   WO 00/47716   *   8/2000

OTHER PUBLICATIONS

Hare, G.M.T., et al., Walking track analysis: a long-term assessment of peripheral nerve recovery. Plastic and Reconstructive Surgery 89: 251-258 (1992).
Hsu, S., et al., Oriented Schwann cell growth on microgrooved surfaces. Biotechnology and Bioengineering 92:579-588 (2005).
Lin., Y., et al., Sciatic nerve repair by microgrooved nerve conduits made of chitosan-gold nanocomposites. Surgical Neurology 70: SI:9-SI:18 (2008).
Nie, X., et al., Improvement of peripheral nervce regeneration by a tissue-engineered nerve filled with ectomesenchymal stem cells. Int. J. Oral Maxillofac. Surg. 36:32-38 (2007).

* cited by examiner

*Primary Examiner* — Anne-Marie Falk
(74) *Attorney, Agent, or Firm* — Baker & McKenzie LLP

(57) ABSTRACT

Implantable nerve regeneration conduits and methods of making the same are disclosed. The implantable nerve regeneration conduits mainly comprise a biodegradable polymer and a metal. Moreover, the conduits may also comprise one or more nerve regeneration enhancing elements, which comprise bioactive molecules or cells. The inner surface of the conduits may be micropatterned photolithographic processes to form microgrooves for facilitating cell alignment.

13 Claims, 5 Drawing Sheets

IMPLANTABLE NERVE REGENERATION CONDUIT

CROSS-REFERENCE TO RELATED APPLICATIONS

This application claims priority to United States Provisional Application No. 61/098,158, filed Sep. 18, 2008, which is incorporated herein by reference in its entirety.

BACKGROUND

1. Technical Field

The disclosures herein relate generally to conduits which are useful as medical devices applicable to neuroregeneration; more particularly, to implantable nerve regeneration conduits for facilitating the regrowth or repair of nervous tissues.

2. Related Art

Nerve injuries are common in clinical practice. According to statistics, more than 90,000 people are affected by nerve injuries every year. While the central nervous system (CNS) is, for the most part, incapable of self-repair and regeneration, the peripheral nervous system (PNS) has an intrinsic ability for repair and regeneration. Studies on the recovery of PNS functionality after injury have become a rapidly growing field dedicated to the searching of suitable ways for facilitating neuroregeneration.

Various approaches have been developed in an attempt to regenerate injured nerves. One such technique involves the actual suturing of the proximal and distal ends of the severed nerve. When a nerve defect of gap is longer, implantation of a graft is often necessary to bridge the stumps for promoting nerve regeneration. Currently, the most widely used material to bridge a peripheral nerve defect is the autologous nerve, e.g., nerve tissue obtained from a second operative site of a patient. However, this treatment raises the possibility of function loss at the donor site, formation of potential painful neuromas, structural differences between donor and recipient grafts, and difficulty in finding a suitable donor site of transplant in patients with diabetic and other chronic diseases, not to mention a potential shortage of graft material where extensive repairs are required.

Therefore, it would be desirable to have an alternative nerve graft material that not only fulfills the requirements, but also overcomes many of the shortcomings, of a nerve autograft. A promising alternative for nerve regeneration which avoids the above-mentioned problems is an artificial graft. In fact, many types of biomaterials, natural or synthetic, have been used to make tubes or conduits for guiding peripheral nerve regeneration.

Conventionally, nerve conduits are made of silicone rubber due to its chemical stability and elastic properties. However, because silicone tubes are non-biodegradable and non-porous, conduits made of silicone rubber often lead to long term complications including fibrosis and chronic nerve compression in clinical applications, and a second surgery is often necessary for removal of the tube or conduit. Accordingly, nerve guide conduits fabricated from biodegradable polymers are preferred over non-biodegradable polymers due to the obvious advantage of eliminating the second surgery to remove the conduits.

The purpose of a resorbable nerve conduit is to provide unperturbed environment for nerve regeneration in short term and to degrade after nerve reconstruction with little tissue reaction. Although a variety of resorbable nerve conduits have been developed, the results thus far are still not satisfactory, and the search for a better conduit is ever ongoing. Therefore, there is a need for an improved nerve conduit for facilitating the regrowth, repair, or regeneration of nervous tissues.

SUMMARY

An implantable nerve regeneration conduit for facilitating the regrowth, repair, or regeneration of nervous tissues is described herein. According to one aspect, the implantable nerve regeneration conduit or device can comprise a polymer which is biodegradable and a metal.

In one preferred embodiment, the polymer can comprise polyglucosamine. More preferably, the polymer can comprise chitosan.

In another preferred embodiment, the polymer can comprise polylactide, such as poly(D-lactide), poly(L-lactide), and poly(D,L-lactide). More preferably, the polymer can comprise poly(D,L-lactide).

To further facilitate nerve regeneration, the conduit may optionally comprise a nerve regeneration enhancing element. The nerve regeneration enhancing element may comprise bioactive molecules or cells. In one preferred embodiment, the nerve regeneration enhancing element can comprise a growth factor, such as fibroblast growth factor 1. In another preferred embodiment, the nerve regeneration enhancing element can comprise cells like Schwann cells or neural stem cells (NSCs). In some embodiments, the cells may be without limitation genetically modified cells. Preferably, the cells comprise in their genome a reporter gene. More preferably, the cells comprise in their genome a gene encoding fluorescent protein. Most preferably, the cells comprise in their genome F1B-GFP gene, which is the green fluorescent protein under the control of human fibroblast growth factor 1 promoter.

In one preferred embodiment, the conduit is made of the mixture of the polymer and the metal. The metal may comprise gold or silver but is not limited thereto. It is believed that the metal may largely enhance the physical strength of the conduit and expedite nerve regeneration. Preferably, the size of the metal is about 1 to about 50 nm in diameter and, more preferably, about 5 to about 30 nm. In some embodiments, the concentration of the metal over the polymer is less than 500 ppm. In one preferred embodiment, the concentration of the metal over the polymer is between about 25 ppm and about 100 ppm.

In another preferred embodiment, the conduit may further comprise an inner surface on which a microgroove is formed. Preferably, the microgroove has a width between about 1 to about 50 micrometer, a spacing between about 1 to about 50 micrometer, and a depth between about 0.1 to about 15 micrometer. More preferably, microgroove has a width between about 10 to about 30 micrometer, a spacing between about 10 to about 30 micrometer, and a depth more than about 0.5 micrometer.

According to another embodiment, an implantable nerve regeneration device comprising a micro-patterned conduit and a nerve regeneration enhancing element is disclosed. Preferably, the micro-patterned conduit can have an inner surface on which a microgroove is formed, the microgroove having a dimension capable of accommodating the nerve regeneration enhancing element.

According to still another embodiment, it is disclosed an implantable nerve regeneration conduit comprising a substantially smooth outer surface and an inner surface on which a microgroove is formed.

According to one embodiment, it is disclosed a method of fabricating an implantable nerve regeneration conduit. The method can comprise providing a composite material comprising a polymer and a metal; forming a micropattern on a substrate; transferring the micropattern to a submaster; casting on the submaster the composite material; and detaching the composite material from the submaster.

These and other features, aspects, and embodiments are described below in the section entitled "Detailed Description."

BRIEF DESCRIPTION OF THE DRAWINGS

The above and other aspects, features and other advantages of the subject matter of the present disclosure will be more clearly understood from the following detailed description taken in conjunction with the accompanying drawings, in which:

FIG. 1 shows the gene expression on non-patterned PLA and micropatterned PLA, where

FIG. 2 shows the dynamic mechanical analysis of chi-Au, where

FIG. 3 shows the effect of chi-Au on proliferation and gene expression of C6 glioma cells and NSC.

DETAILED DESCRIPTION

Figure 1A:
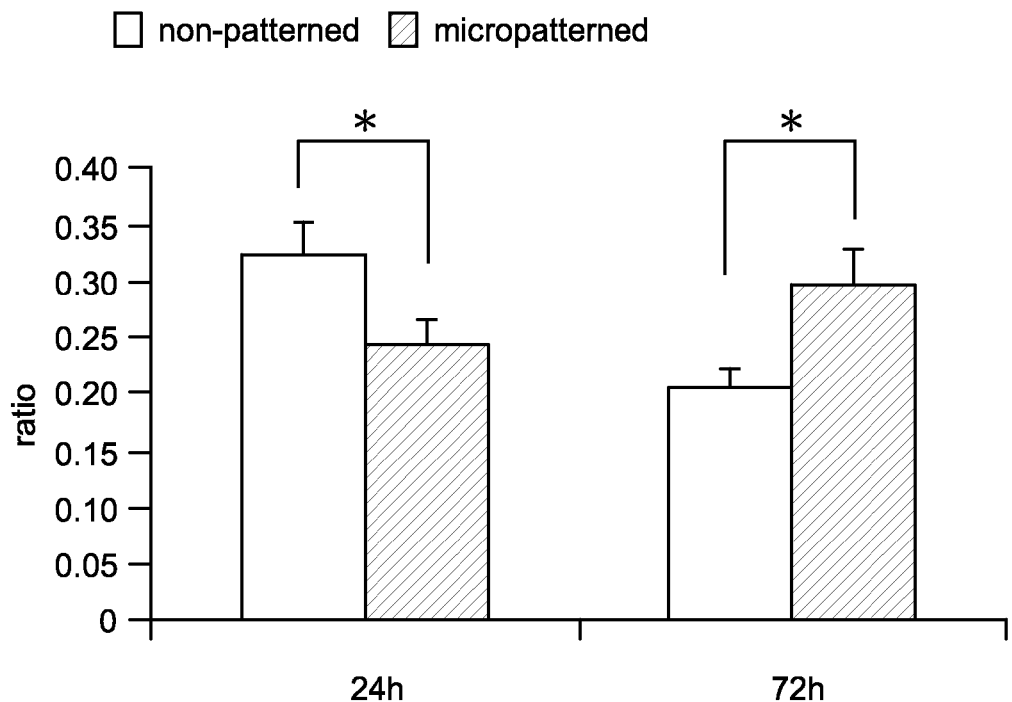
FIG. 1A illustrates the expression of NGF gene.

The disclosures herein relate generally to conduits useful as medical devices for facilitating the regrowth or repair of nervous tissues. In some embodiments, the conduits can comprise a porous or non-porous tubular structure having a first end and a second end, a wall of a substantially uniform thickness, and a channel which is defined by the wall and is extending from the first end to the second end of the tubular structure. In other embodiments, however, the conduits can be non-tubular devices as well.

In order to obviate the necessity of a second surgery for removal of the tube or conduit, it is preferred that the conduits are biodegradable and can be degraded to lower molecular weight fragments which can be absorbed and cleared by the host. Examples of such biodegradable materials include without limitation various types of alginate gel, polyphosphoester, collagen, gelatin, polyglycolide, polysaccharide, glycosaminoglycan, polylactide, polyglucosamine, and derivatives or mixtures thereof.

In addition to the biodegradable materials, the conduits of some embodiments may optionally further comprise a metal capable of enhancing the physical strength of the conduit or facilitating nerve regeneration. Preferably, the metal may be but not limited to gold or silver. In some embodiments, the size of the metal ranges from about 1 to about 50 nm in diameter. In preferred embodiments, the size of the metal ranges from about 5 to about 30 nm.

The concentration of the metal over the polymer, which is believed to be correlated to the size of the metal, is generally less than 500 ppm. Preferably, the concentration of the metal over the polymer is between about 25 ppm and about 100 ppm. In one embodiment where the average size of metal is about 5 nm, the preferable concentration is between about 20 ppm and about 150 ppm. In another embodiment where the average size of metal is about 50 nm, the preferable concentration is above about 50 ppm.

In some embodiments, the conduit may optionally be seeded or filled with a nerve regeneration enhancing element. Examples of such element include various kinds of bioactive molecules, such as neurotrophic factors, growth factors, bioadhesive molecules like laminin, and alignment-promoting molecules. Additionally, the nerve regeneration enhancing element may also be cells. For example, fibroblasts, Schwann cells, neural stem cells, and neural progenitor cells are all applicable to the embodiments. Furthermore, the cells used may be further genetically modified. For example, they may comprise in their genome a reporter gene, such as a gene encoding fluorescent protein. Methods for the preparation of the transgenic cells are described in U.S. Pat. Nos. 6,984,518 and 7,045,678 and U.S. pending patent application Ser. No. 11/375,889, which are incorporated herein by reference in its entirety as if set forth in full.

To facilitate cell alignment during nerve regeneration, microgrooves may be fabricated on the inner surface of the conduits of some embodiments. The microgrooves can be transferred from the micropatterned silicon formed by the adaptation of the photolithographic technique and etching process. In some embodiments, the microgrooves are formed at separated locations and have a structure suitable for accommodating the nerve regeneration enhancing element or for facilitating nerve regeneration. Preferably, the microgrooves have a width between about 1 to about 50 micrometer, a spacing between about 1 to about 50 micrometer, and a depth between about 0.1 to about 15 micrometer. More preferably, the microgrooves have a width between about 10 to about 30 micrometer, a spacing between about 10 to about 30 micrometer, and a depth more than about 0.5 micrometer.

The following examples are for purposes of illustration only and are not intended to limit the scope of the claims which are appended hereto.

EXAMPLE 1-1

Fabrication of Micropatterned Polylactide

Methods of making micropatterned silicon are described in Hsu et al., "Oriented Schwann Cell Growth on Microgrooved Surfaces. Biotechnology and Bioengineering. 92(5), 579-588," which is incorporated herein by reference in its entirety as if set forth in full. The negative photoresist (SU-8 2005, MicroChem, USA) was coated onto the p-type silicon wafer at 3000 rpm using a spin coater (Branchy Technology, Taiwan). The wavelength of the exposure system (ABM Aligner, USA) was 365 nm (I-line), and the exposure time was 12 seconds. The width/spacing size of the mask was 20 µm/20 µm. The unreacted photoresist was removed to achieve microgrooves of a 3 µm depth on the silicon wafer (silicon/crosslinked SU-8 2005).

Several poly(dimethylsiloxane) (PDMS) submaster molds were created by pouring Dow Corning Silastic MDX4-4210 on the patterned silicon wafer, to facilitate the mold release of the micropatterned polymer after the pattern transfer process. The micropattern was transferred from the PDMS submasters to the biodegradable polymer. The solution of 20% poly(D, L-lactide) (8300D, Cargill Dow, USA) (PLA) in 1,4-dioxane solvent were prepared. The polymer solutions were cast on the PDMS submasters. After being air-dried for 24 h, the polymer substrates were then immersed in alcohol for 24 h and detached from the PDMS submasters. The micropatterns were examined under the optical microscope and SEM for their quality. The precision of the groove depth was confirmed by the High Performance Surface Metrology (P-10, KLA-Tencor, USA).

EXAMPLE 1-2

Culture of Neural Stem Cell

Mouse brains from two-month old were minced with a scalpel and gently triturated through a series of descending-diameter, fire-polished Pasteur pipets to make a single-cell suspension. Minced cells were seeded in 35-mm diameter culture dishes (1000 viable cells per plate) without supplementary substrate or adhesion factors in DMEM/F-12 (1:1) medium containing 10% FBS (Giboco, USA). After two days, most cells died. Approximately 10-20 cells per plate (×4 plates) underwent cell division. Cells were trypsinized, pooled together and continued dividing another 2-3 days. At 6 to 8 days, neurosphere of proliferating cells were formed and then transferred to poly-L-ornithine-coated multi-chamber slides. Cells were transfected with F1B-GFP on a two-day interval to determine a time point that could achieve the highest percentage of GFP-positive cells. The stable cell lines were obtained by selection with 200 µg/ml Geneticin (Gibco, 11811, USA). The Geneticin-resistant mouse neural stem cells were pooled (approximately 30 colonies per plate), and expanded. GFP-positive mouse NSC were enriched using a fluorescence activated cell sorter (FACS Aria, BD Biosciences, Palo Alto, Calif., USA) two to three times until greater than 95% purity was achieved.

NSC were cultured in DMEM/F12 supplemented with 10% FBS, 200 µg/ml Geneticin, 20 ng/ml human FGF1 and streptomycin-penicillin (100 U/ml). The inclusion of FGF1 helps preserve the multipotency of neural stem cells. Thus, GFP expression in the GFP-positive cells will last for six weeks in the presence of FGF1 whereas, in the absence of FGF1, the GFP expression will last for only three weeks. Cultures were incubated in a humidified incubator with 5% $CO_2$ at 37° C. The medium was refreshed twice weekly.

EXAMPLE 1-3

F1B-GFP Plasmid DNA and Transfection

To construct the F1B-GFP plasmid DNA, the 589-bp SmaI-HindIII fragment that contains the brain-specific promoter of FGF1 was isolated from F1B-Tag plasmid and cloned into XhoI-HindIII sites of pEGFP-1. XhoI site was blunt-ended with Klenow fragment before it was ligated to the SmaI site. The resultant 4733-bp F1B-GFP plasmid DNA was sequenced to confirm its identity. Plasmid pEGFP-1 was purchased from BD Biosciences Clontech. F1B-GFP plasmid DNA was transfected into mouse brain cells with Lipofectamine® (Invitrogen) according to the manufacture's protocol. G418-positive cells were selected at a concentration of 200 µg/ml Geneticin as pEGFP-1 contains a neomycin-resistant cassette. The mouse brain cells thus selected are considered neural stem cells as they formed neurospheres and could be induced to differentiate into all three types of neural progenies including neurons, astrocytes and oligodendrocytes. Since F1B promoter is active in the neural stem cells, it provides a facile means to select for neural stem cells based on the positive expression of GFP.

EXAMPLE 1-4

Proliferation and Alignment of NSC on Micropatterned PLA

The substrates were cut as 15 mm disks and placed into the bottom of 24-well culture plate. The substrates were then sterilized by 70% alcohol solution for 15 min and rinsed with PBS. Cells (~1×10$^4$ cells/well) were seeded onto the substrates. To evaluate cell attachment and proliferation, cells were trypsinized at 24, 48 or 72 h and the number was determined by trypan blue exclusion using a hemocytometer combined with an inverted phase contrast microscope (Nikon TE-300, Japan).

Cell alignment was evaluated at 24 h and 72 h after culture. The GFP expression of live NSC on the substrate could be directly viewed under a fluorescence microscope (Nikon Eclipse 80i, Japan). To quantify the cell alignment, cells on the substrates were fixed and stained with methylene blue. The orientation angle was determined by examining the cells in nine different areas under a reflective microscope (Nikon Labophot, Japan) using an image analysis system (Image-Pro Lite, Media Cybernetics, USA). The cells were fitted with ellipses. The angle created by the major axis and the direction of grooves was defined as the orientation angle. The data were imported into Microsoft Excel to create the distribution of the angle (frequency plot). Those cells with an orientation angle between −10 and 10 degree (°) were identified as aligned cells. The percentage of alignment was defined as the fraction of aligned Schwann cells (±10°) over the whole population in the frequency distribution.

For cytoskeleton observation, cells on the test substrates were fixed in 4% paraformaldehyde/PBS at room temperature. After fixation, the samples were washed with PBS and added the permeabilising buffer at room temperature. The samples were stained by the addition of rhodamine conjugated phalloidin (1:500 in PBS, Sigma, USA) at room temperature. The samples were washed, and 4,6-diamidino-2-phenylindole dihydrochloride (DAPI, 1:500 in PBS, Sigma, USA) was added at room temperature to stain cell nuclei. Finally, the samples were viewed by the fluorescence microscope. The half-life of GFP was determined in cultured mouse cells to be about 26 h. Therefore, when tracing GFP expression in wounded sciatic nerves for several weeks, there is minuscule GFP expression to be traced in differentiated neurons.

EXAMPLE 1-5

Gene Expression of NSC Cultured on Micropatterned PLA

Expressions of the nerve growth factor (NGF) and brain-derived neurotrophic factor (BDNF) genes were detected by the following steps. Total RNA at 24 or 72 h was extracted by Trizol reagent (15596-018, Invitrogen, India) after the cells were trypsinized. Five µg of total RNA was reverse-transcribed with the first-strand cDNA synthesis kit (Fermentas, USA). One µl of the cDNA reaction mixture was used in each PCR reaction. PCR was carried out in a GeneAmp PCR system 2700 thermal cycler (ABI, USA) for 35 cycles. Cycling parameters were 94° C. for 30 sec, after that, 56° C. for 30 sec, and than 72° C. for 30 sec, followed by a final extension at 72° C. for 10 min. PCR primers for β-actin were used to confirm the fidelity of the PCR reaction and as an internal control for the semi-quantitative analysis. The amplified products were analyzed by electrophoresis on 1.5% agarose-TAE [10 mM Tris (pH 7.5), 5.7% glacial acetic acid, and 1 mM EDTA] gels and visualized by ethidium bromide staining.

EXAMPLE 1-6

Animal Implantation of the Micropatterned Nerve Conduits

The micropatterned PLA substrates were rolled into conduits using a 1.5 mm-diameter mandrel, and the edges were adhered tightly by a small amount of solvent. Conduits were checked for their fidelity and sectioned into 12 mm segments before implantation.

NSC (~5×10$^4$ cells/ml, about 30 μl) were seeded on the micropatterned conduit using a roller (~1 rpm) previously designed for seeding endothelial cells on vascular grafts (Hare et al., "Walking track analysis: a long-term assessment of peripheral nerve recovery", Plast. Reconstr. Surg. 89, 251-258). After 24 h and 72 h, the conduits were carefully fixed and cut in longitudinal direction for observation of NSC alignment in the lumen surface.

Fourteen male Sprague-Dawley rats weighing 250-300 g were used for the preliminary animal studies. They were divided into two experimental groups and two control groups. The two experimental groups (n=4) received micropatterned conduits (1.95 mm ID, 0.49 mm in wall thickness, and 12 mm long), seeded with NSC (72 h) or without NSC. The two control groups (n=3) received silicone tubes (Silastic, RX50, Dow Corning, USA; 1.57 mm ID, 0.84 mm in wall thickness, and 12 mm long) and reversed autografts (10 mm long).

The animals were housed in standard laboratory cages under temperature-controlled conditions at 22±1° C., with a 12-hour light cycle, with free access to standard rat chow and water. The surgery was performed with animals under general anesthesia with intraperitoneal injection of Citosol (6 mg/100 g) throughout the surgical procedures. For each rat, surgery was conducted on the left hind leg, under aseptic conditions. After an incision had been made in the skin, the sciatic nerve was exposed by making a muscle splitting incision. A 10 mm nerve segment was excised with microscissors. The reversed autograft or the conduit was interposed into the 10 mm nerve defect. The proximal nerve was anchored in the conduit by 7-0 nylon microsutures. The distal end was then sutured into the other end of the conduit. Nerve stumps at both ends were sutured into the conduit to a length of approximately 1 mm. The wound was then closed in layers using 3-0 Dexon sutures.

The sciatic functional index (SFI) that assessed the functional muscle reinnervation was calculated based on the walking track analysis, by the equation SFI=−38.3(PLF)+109.5 (TSF)+13.3(ITF)−8.8, where PLF (print length function)=(experimental PL−normal PL)/normal PL, TSF (toe spread function)=(experimental TS−normal TS)/normal TS (1st to 5th Toe), and ITF (inter-median toe spread function)=(experimental IT−normal IT)/normal IT (2nd to 4th Toe) (Nie et al., "Improvement of peripheral nerve regeneration by a tissue-engineered nerve filled with ectomesenchymal stem cells", Int. J. Oral Maxillofac Surg. 36, 32-38). Six weeks after implantation, the rats implanted with conduits or controls were euthanized in a $CO_2$ chamber. The tissues were harvested and histologically analyzed. Specimens were fixed overnight in 4% paraformaldehyde, stained with 1% osmium tetroxide (Polysciences, PA, USA) and embedded in paraffin. The specimens was thin-sectioned (cross-sectional, 4 μm) and stained with H&E or toluidine blue. The embedded stained nerve sections were placed on the stage of a microscope. The images of the histological sections at the midconduit were digitized by a digital camera (Nikon Coolpix 4500, Japan). The number and areas of individual myelinated axons at the midconduit were determined using an image analysis system (Image-Pro Lite, Media Cybernetics, USA). The number of blood vessels was also counted.

Data from the experiments were expressed as mean±standard deviation (n=3-6). Statistical differences were analyzed by one-way analysis of variance (ANOVA). p<0.05 was considered as statistically significant.

Figure 1B:
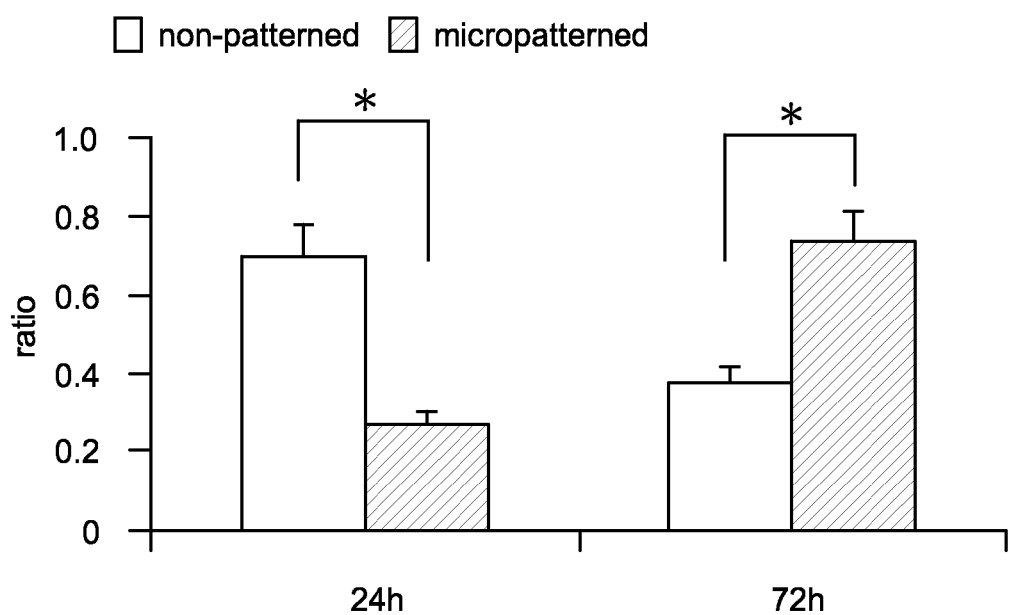
FIG. 1B illustrates the expression of BDNF gene.

The lateral dimensions of the microgrooves were about 21±0.5/19±0.5 μm (n=3). The surface metrological data showed that the depth of the microgrooves on PLA was uniform at 3.0±0.1 μm (n=3). The fabrication process was successfully controlled to make reproducible micropatterned substrates. The NSC have already attached to the substrate at 24 h. There was no statistically significant difference in cell number on non-patterned or micropatterned substrates. The cell number approximately doubled at 48 h and increased about six folds at 72 h for both substrates. The NSC expressed GFP at all time, i.e. remained undifferentiated. The quantitative analysis of cell orientation on the micropatterned substrate showed that at 24 h 74.5±7.5% of NSC were aligned and at 72 h 84.7±8.2% of NSC were aligned (n=3 for each time point). The orientation of actin microfilaments on the micropatterrned PLA was observed whereas no bias was found in the orientation of the cytoskeleton on the non-patterned PLA. FIG. 1 shows the semi-quantitative analysis of NGF gene expression (FIG. 1A) and BDNF gene expression (FIG. 1B). At 24 h cells expressed NGF and BDNF genes at higher levels on non-patterned PLA than on micropatterned PLA. However at 72 h, NSC on micropatterned surfaces had higher gene expressions for NGF and BDNF.

After the rolling procedure, the micropattern on the lumen surface of the conduits remained visible with the featured dimensions well kept. The NSC seeded by the rotational method were properly aligned on the internal surface of the conduit at 24 h and 72 h.

No animals died after six weeks of implantation process. In the occasion that the nerve was successfully connected, the newly regenerated nerve in a form of thin white tubular substance that connected the two ends could be visualized after the nerve conduit was longitudinally cut open by microscissors. As shown in Table 1, the success rate (the percentage of animals with the mentioned successful connection) was 75% in micropatterned PLA conduits alone, and 100% in the micropatterned PLA conduits seeded with NSC.

TABLE 1

Success rate and sciatic functional index (SFI) in the rat sciatic nerve repair model

|  | Success rate | SFI before sacrifice |
| --- | --- | --- |
| Micropatterned PLA conduits | 3/4 | −69 ± 10 |
| Micropatterned PLA conduits with NSC | 4/4 | −47 ± 10* |
| Silicone tube | 1/3 | −77 ± 9 |
| Autograft | 3/3 | −79 ± 7 |

*p < 0.05, greater than other groups.

The low success rate of the silicone control (33%) and the high success rate of the autograft control (100%) were both expected. As shown in Table 2, image analysis of the histological sections at the midconduit showed that the micropatterned PLA conduits seeded with NSC had significantly more myelinated axons than the non-seeded group (1856±315 vs. 829±165, p<0.05). The mean area of each axon was also greater (9.4±1.8 μm$^2$ vs. 6.5±1.3 μm$^2$, p<0.05). Both had good number of vessels, indicating the ongoing nerve repair. The autograft group had a similar performance to the conduits seeded with NSC, in the numbers of axons and vessels, as well as the mean area of axons. The SFI from walking track analysis (Table 1) during 5 to 6 weeks before sacrifice also supported the histological data. The SFI was higher for the micropatterned PLA conduits with NSC than the conduits alone (−47±12 vs. −69±10, p<0.05). The SFI values of the two control groups were not significantly different from that of the conduits alone, in spite of the better histological outcome of the autograft group. From the representative histological sections of explanted PLA conduits, compared to those of the autograft and the normal nerve, it was evident that the PLA conduit seeded with NSC or the autograft contributed to morphology more resembling to that of the normal nerve.

TABLE 2

Quantitative data from the histological analysis of the cross-section at the midconduit

| | Mean area of axons ($\mu m^2$) | Number of myelinated axons | Number of blood vessels |
|---|---|---|---|
| Micropatterned PLA conduits | 6.5 ± 1.3* | 829 ± 165* | 40 ± 9 |
| Micropatterned PLA conduits with NSC | 9.4 ± 1.8 | 1856 ± 315 | 48 ± 11 |
| Autograft | 10.3 ± 2.5 | 1905 ± 371 | 58 ± 13 |

*p < 0.05, smaller than other groups.

In addition to the PLA conduit mentioned above, other materials may also be used in the embodiments described herein, like those described in Lin et al., "Sciatic nerve repair by microgrooved nerve conduits made of chitosan-gold nanocomposites. Surgical Neurology," published on Apr. 25, 2008, which is incorporated herein by reference in its entirety as if set forth in full.

EXAMPLE 2-1

Preparation of Chi-Au Nanocomposite Materials

One percent chitosan (Sigma, St Louis, Mo.) solution was dissolved in 0.5 mol/L acetic acid for 12 hours at room temperature. The gold nanoparticles in solution were supplied by Global NanoTech, Taipei, Taiwan. The solution contained pure-gold fine particles (5 nm) in water (50 ppm/mL). After filtering the chitosan solution, a certain amount of gold nanoparticle solution was added; so the final concentration in the polymer was 25, 50, or 100 ppm. To make the substrates for biological tests, 100 µL of the chi-Au solution was coated onto coverslips (15-mm diameter; Matsunami, Osaka, Japan) and air-dried for 48 hours.

EXAMPLE 2-2

DMA of Chi-Au Materials

Changes in dynamic properties of chi-Au materials were examined by DMA using a TA Instruments DMA 2980 (New Castle, Del.). To prepare the samples for mechanical testing, chi-Au solution was cast on a glass mold and peeled after being dried. Sample strips with a geometry of about 30 mm long×5.0 mm wide×0.07 mm thick were run in tension at 1 Hz and an amplitude of 10 µm. Samples were mounted in the DMA at room temperature and then run from 30° C. to 220° C. at a ramp rate of 5° C./minute. The dynamic modulus was expressed as storage modulus (in megapascals), and the tendency to dissipate energy was indicated by the parameter tan δ.

EXAMPLE 2-3

Cell Maintenance

Rat glioma cell line C6 (BCRC-860046; Bioresources Collection and Research Center, Hsinchu, Taiwan) and murine NSC were applied for in vitro tests. The NSC were isolated from 2-month-old mouse brain and were transfected with F1B-GFP (U.S. Pat. Nos. 6,984,518 and 7,045,678). The stable cell lines were obtained by selection with 200 µg/mL Geneticin (11811; Gibco, Los Angeles, Calif.). The Geneticin-resistant NSC were pooled and expanded. The GFP-positive mouse brain cells were enriched using fluorescence-activated cell sorter (FACS Aria; BD Biosciences, Palo Alto, Calif.) repeatedly until greater than 95% purity was reached. The C6 cells were cultured in DMEM supplemented with 44 mmol/L NaHCO3 (Sigma), 10% FBS, streptomycin-penicillin (50 U/mL), and 1% sodium pyruvate (59203-100M; JRH, Lenexa, Kans.). DMEM/F12 (11330, Gibco, Carlsbad, Calif.) supplemented with 10% FBS, 200 µg/mL Geneticin, 20 ng/mL human FGF1, and streptomycin-penicillin (100 U/mL) was used for NSC culture medium. Cultures were incubated in a humidified incubator with 5% $CO_2$ at 37° C. The medium was refreshed twice weekly.

EXAMPLE 2-4

Assessment of Cell Proliferation

Before seeding the cells, the composite substrates on coverslips were soaked in 70% ethanol, rinsed with PBS, and then placed into 24-well culture plates. To assess the effect of gold nanoparticles at different concentrations, cells at a density of $10^4$ per well for C6 and $5×10^4$ per well for NSC were seeded. The cell number was counted at 24, 48, and 72 hours by the hemocytometer.

EXAMPLE 2-5

Gene Expression of Neurotrophic Factors

Total RNA was extracted from C6 or NSC grown on chi-Au nanocomposites after culture for 72 hours. Trizol reagent (15596-018; Invitrogen, Carlsbad, Calif.) was added after the cells were trypsinized. Five micrograms of total RNA was reverse-transcribed with the first-strand cDNA synthesis kit (Fermentas, St Leon-Rot, Germany) following the manufacturer's instructions. Polymerase chain reaction was performed in a 25-µL reaction volume containing 1 µL of the cDNA, 0.5 µL of 10 µmol/L each primer (Table 3), and 5 µL of 5×PCR Master Mix buffer (Gene Mark, Tainan, Taiwan). Polymerase chain reaction was carried out in a GeneAmp PCR system 2700 thermal cycler (ABI, Foster Calif., USA). The cycling parameters of cDNA were 35 cycles of 94° C. for 30 seconds, 55° C. for 30 seconds, and 72° C. for 30 seconds, followed by a final extension at 72° C. for 7 minutes. β-Actin was used to confirm fidelity of the PCR reaction and as an internal control for semiquantitative analysis. The amplified products were analyzed by electrophoresis on 1.5% agarose-TAE (10 mmol/L Tris [pH 7.5], 5.7% glacial acetic acid, and 1 mmol/L EDTA) gels and visualized by ethidium bromide staining.

TABLE 3

Primers for the PCR reaction

| Gene | Sequence | Size (base pairs) |
|---|---|---|
| BDNF | F- GAC TCT GGA GAG CGT GAA T<br>R- CCA CTC GCT AAT ACT GTC AC | 325 |
| NGF | F- ACC TCT TCG GAC ACT CTG GA<br>R- GTC CGT GGC TGT GGT CTT AT | 168 |
| GDNF | F- CCC GAA GAT TAT CCT GAC CA<br>R- TAG CCC AAA CCC AAG TCA GT | 242 |
| β-Actin | F- TCC TGT GGC ATC CAC GAA ACT<br>R- GGA GCA ATG ATC CTG ATC TTC | 185 |

EXAMPLE 2-6

Fabrication of Microgrooves on Chi-Au

Photolithographic techniques were used to fabricate silicon wafers with the desired micropatterns that were then transferred to the PDMS submaster by casting PDMS on the silicon wafer. To transfer microgrooves on the chi-Au substrates, the solution containing 50 ppm gold nanoparticles was cast on the PDMS submasters. After being air-dried, the substrates were then immersed in alcohol and detached from the PDMS submasters. To study the physical guidance of NSC on micropatterned chi-Au substrates, the pattern dimensions were 20/20/3 μm (groove width/spacing/depth).

EXAMPLE 2-7

Cell Alignment

To evaluate cell alignment, the cultured NSC ($3 \times 10^4$ cells per square centimeter) on the substrates were examined at 24 and 72 hours after culture. After staining with methylene blue, the orientation of the NSC on the substrates was measured quantitatively using an image analysis system (Image-Pro Lite; Media Cybernetics, Silver Spring, Md.). Those cells with an orientation angle between $-10°$ and $10°$ were identified as the aligned cells, and the proportion of the aligned cells in the population was calculated. Control data were taken from measurements made on NSC on nonpatterned chi-Au substrates.

EXAMPLE 2-8

Cytoskeleton Observation

To evaluate the cytoskeleton of NSC on the substrates, cells cultured after 24 and 72 hours were fixed in 4% paraformaldehyde. After several rinses with PBS, 500 μL of 0.5% Triton X-100 (t-octylphenoxypolyethoxyethanol; Sigma, T9284) was added for 10 minutes. The samples were rinsed, and 300 μL of 0.03% phalloidin (P2141, Sigma) was added in the dark for 30 minutes. To stain the cell nuclei, cells were rinsed; and 300 μL of 0.01% DAPI (D9542, Sigma) was added in the dark for 30 minutes. Samples were rinsed and then mounted onto microscope slides. The cytoskeleton was observed by the fluorescence microscope (Eclipse 80i; Nikon, Tokyo, Japan).

EXAMPLE 2-9

Conduits for Implantation

The micropatterned substrates were rolled into conduits by a 1.5-mm-diameter glass mandrel and adhered by a small amount of chitosan solution. Conduits with 1.95-mm internal diameter and 2.22-mm external diameter were sectioned into 12-mm-long segments. The suspension of GFP-positive mouse NSC ($5 \times 10^4$/mL) was injected into the conduit, and then the conduit was sealed immediately at both ends and rotated at 1 rpm for 72 hours before implantation.

The structure of microgrooved conduit (without cell seeding) was imaged using SEM. After mounting, conduits were gold-coated using a Hitachi coating unit IB-2 coater. Coated samples were examined by a scanning electron microscope (S-3000N, Hitachi, Tokyo, Japan).

EXAMPLE 2-10

Animal Implantation of Microgrooved Nerve Conduits

Nine male Sprague-Dawley rats weighing 250 to 300 g were used for the preliminary animal test (n=3 for each group). The two experimental groups received the grooved surface conduits seeded with and without NSC, respectively. The other group received reversed autografts and served as controls. The animals were housed in standard laboratory cages under temperature-controlled conditions at $24°$ C.$\pm 1°$ C. and 45% humidity with 12-hour light cycles, with free access to standard rat chow and water. All procedures followed the guidelines for the animal care, and the Ethical Committee of National Chung Hsing University had approved the experiment.

Animals were anesthetized with Citosol (6 mg/100 g intraperitoneally (Shinlin Sinseng Pharmaceutical Co, Taipei, Taiwan)), and the left hind legs were used to perform the surgery. A skin incision from the left knee to the hip was made to expose the underlying muscles, which were then retracted to reveal the sciatic nerve. The microgrooved conduit, with or without GFP-positive mouse NSC, or the reversed autograft was interposed into the 10-mm sciatic nerve defect. The nerve stumps were anchored inside to a length of approximately 1 mm of the conduit by 7-0 nylon microsutures. The operation site was sutured in layers using 3-0 Dexon (Unik Surgical Sutures MFG Co, Taipei, Taiwan). Six weeks after implantation, the rats implanted with conduits or controls were euthanized.

EXAMPLE 2-11

Functional Assessment of Nerve Regeneration

Walking track analysis was performed after 3 and 6 weeks. For the calculation of SFI, the following footprint parameters were measured: the distance to the PL, TS, and IT. Data were collected for both the N and the E hind legs. The SFI was calculated based on the aforementioned formula. An index of zero reflected normal function, and $-100$ theoretically represented complete loss of function.

EXAMPLE 2-12

Histologic Analysis

The tissues were harvested, fixed overnight in 4% paraformaldehyde, stained with 1% osmium tetroxide (Polysciences, Warrington, Pa.), embedded in paraffin, thin-sectioned (4 μm), and stained with toluidine blue. The number of myelinated axons and the regenerated area were determined using an image analysis system (Image-Pro Lite, Media Cybernetics). The number of blood vessels was also counted.

Figure 2A:
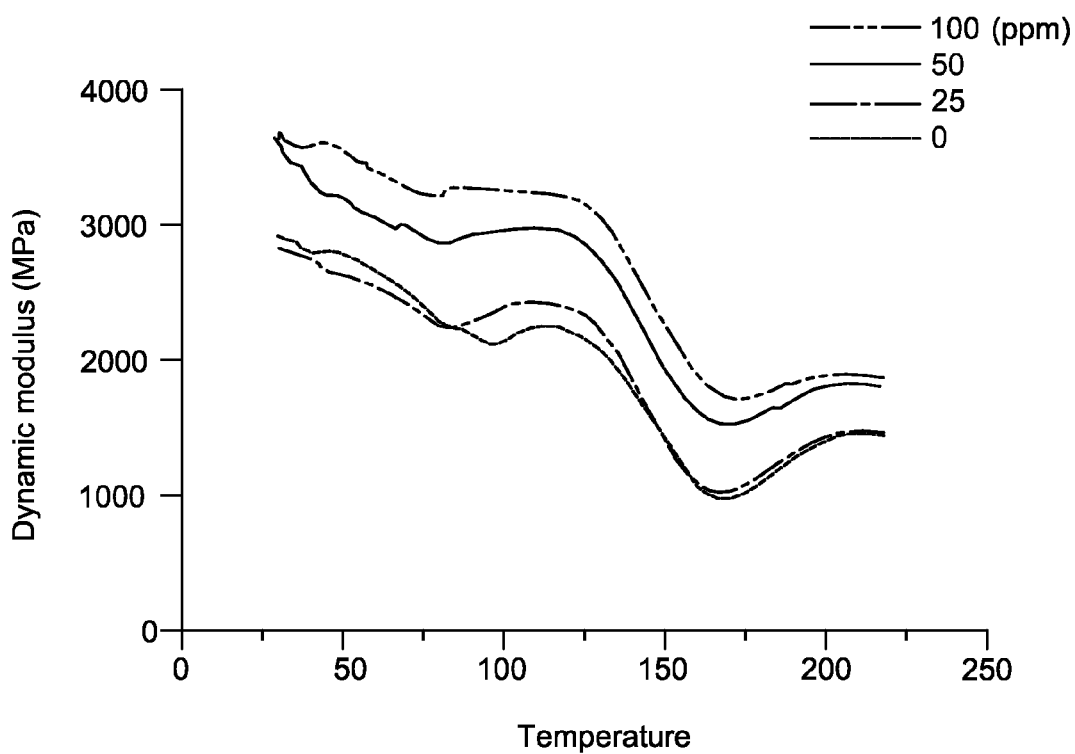
FIGS. 2A and 2B illustrate the dynamic modulus and tan 6 of the materials, respectively.
Figure 2B:
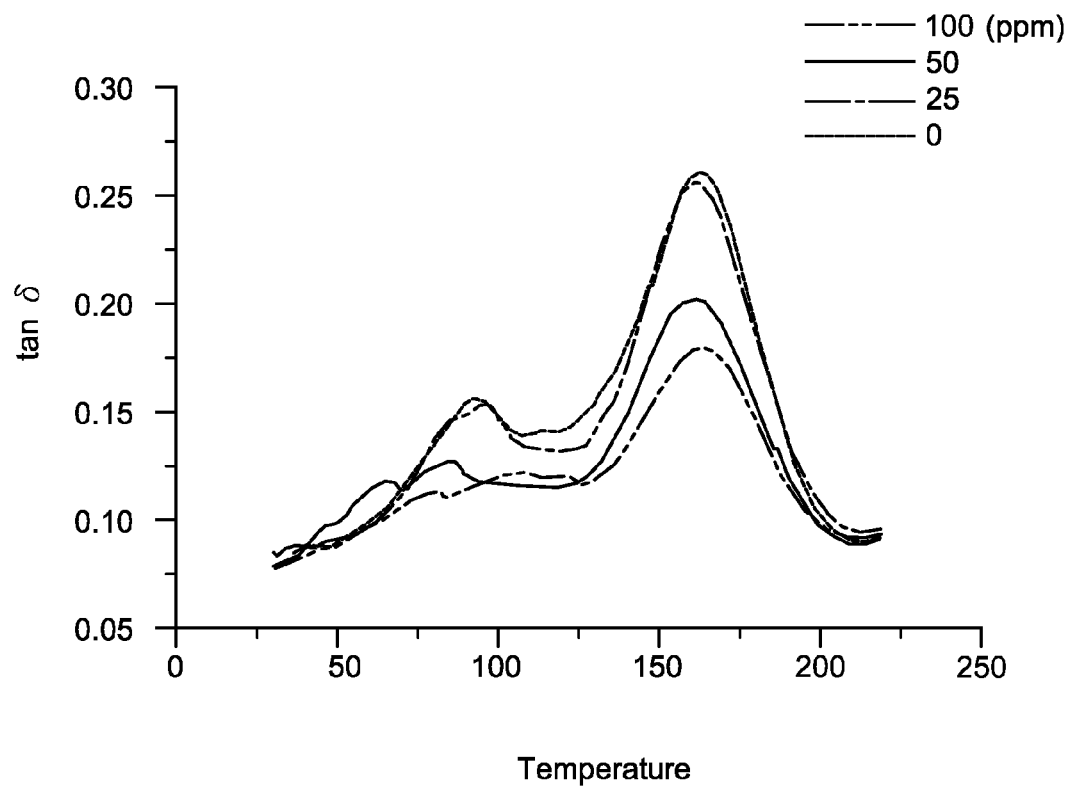

The dynamic mechanical properties of chi-Au were investigated using DMA. Refer to FIG. 2 for the dynamic mechanical analysis of chi-Au, where FIGS. 2A and 2B illustrate the dynamic modulus and tan δ of the materials, respectively; in addition, refer to Table 4 for the storage modulus and glass Tg of the materials. From the overlay of DMA scans on individual chi-Au concentration, there was a concentration-dependent increase in the dynamic modulus except for the values of 25 ppm before 82° C., which were slightly lower than those of 0 ppm. At 37° C., the dynamic modulus was 2787 MPa at 25 ppm, whereas it was 2830 MPa at 0 ppm. The overall patterns were similar at 0 and 25 ppm. At 50 ppm, there was a higher dynamic modulus compared with 0 and 25 ppm. Chitosan with 100 ppm gold, as expected, was a strong material, as could be seen by the highest dynamic modulus (FIG. 2A, Table 4). Chitosan-gold 0 and 25 ppm had higher tan δ than chi-Au 50 and 100 ppm. Glass Tg indicated by the peak of tan δ was slightly reduced at 50 ppm (FIG. 2B, Table 4).

TABLE 4

Dynamic mechanical properties of chi-Au

| ppm | Storage modulus (MPa) (37° C.) | Tg (fsC) |
|---|---|---|
| 0 | 2830 | 161.60 |
| 25 | 2787 | 160.86 |
| 50 | 3456 | 160.43 |
| 100 | 3593 | 162.88 |

Figure 3A:
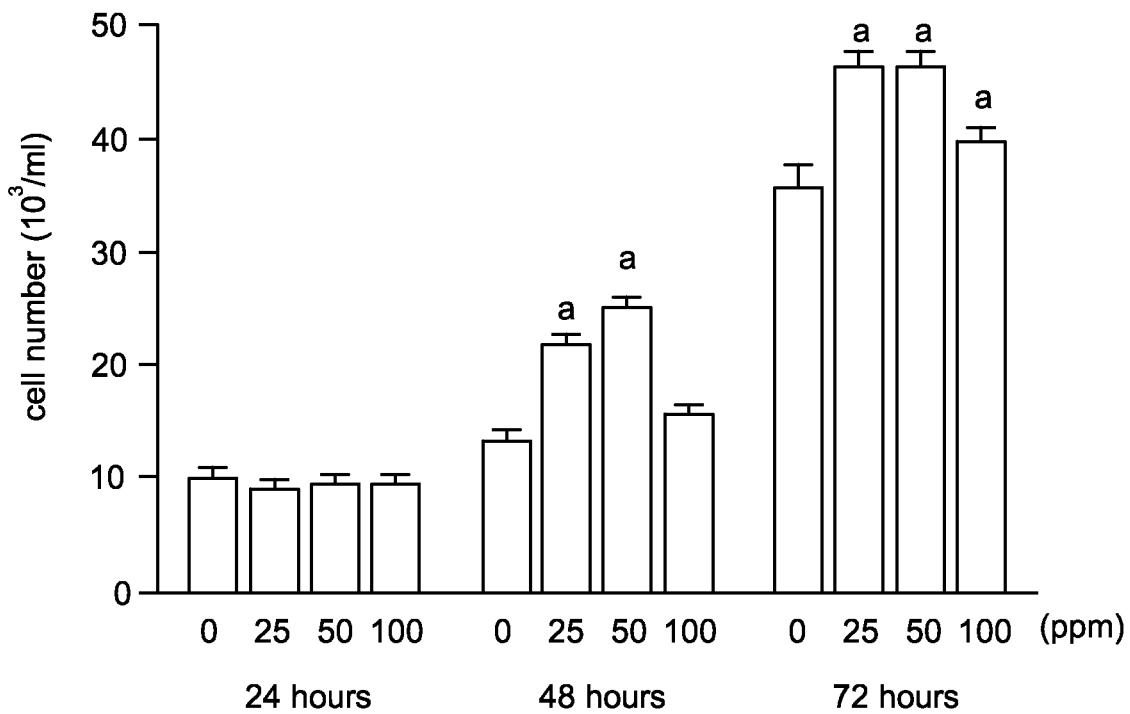
FIG. 3A—C6 proliferation.
Figure 3B:
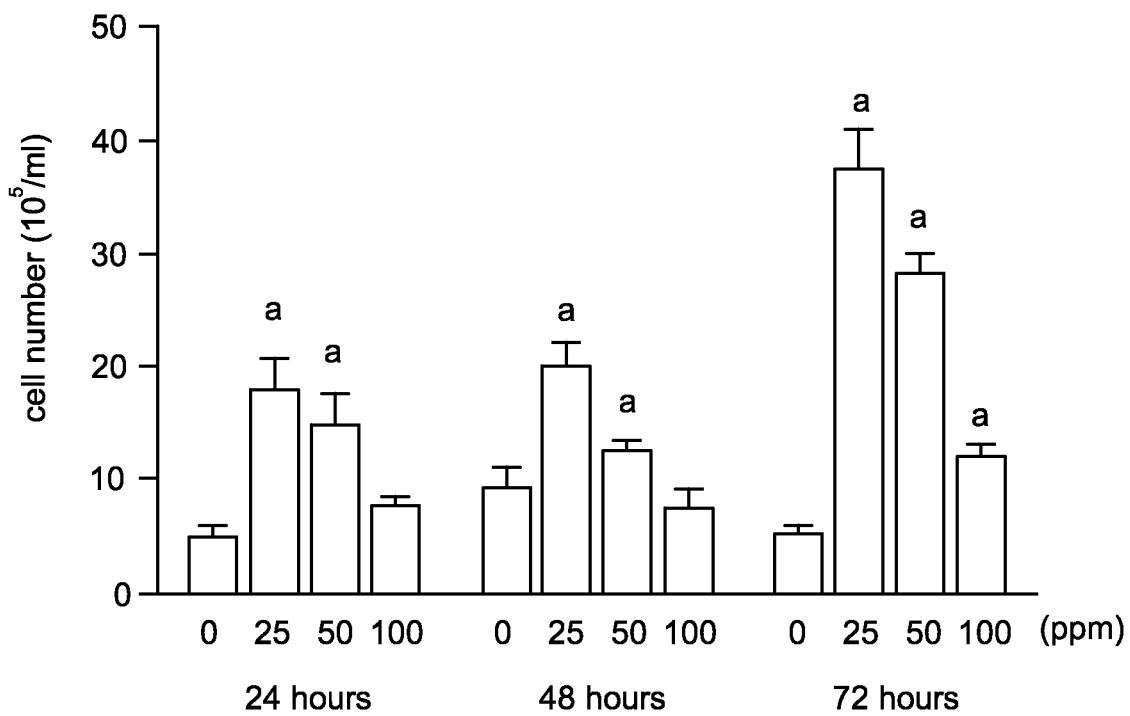
FIG. 3B—NSC proliferation.

The cytocompatibility of different chi-Au composites was tested in vitro by analyzing cell proliferation and gene expression of both C6 cells and NSC. As shown in FIGS. 3A and 3B, gold nanoparticles had a stimulatory effect on cell proliferation that was concentration dependent. For NSC, cell proliferation was significantly increased, compared with the control (0 ppm), at the concentration of 25 or 50 ppm. However, when the gold concentration was increased to 100 ppm, cell proliferation was similar to the control. Results showed that the nanocomposites containing 25 or 50 ppm were superior to those at other concentrations in the proliferation of both C6 and NSC.

Figure 3C:
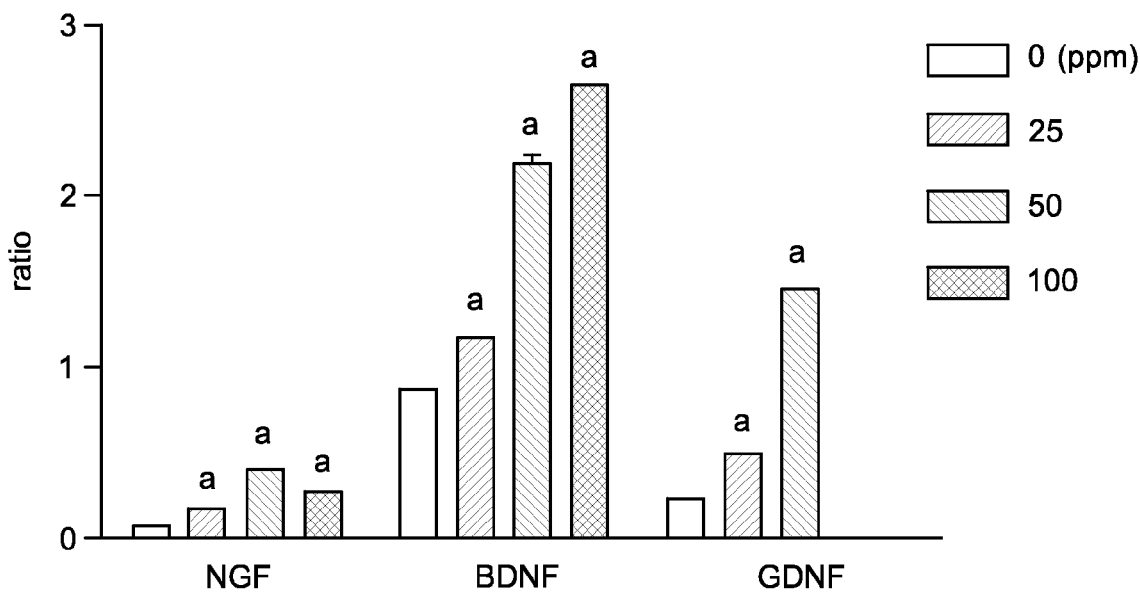
FIG. 3C—gene expression in C6 glioma cells.
Figure 3D:
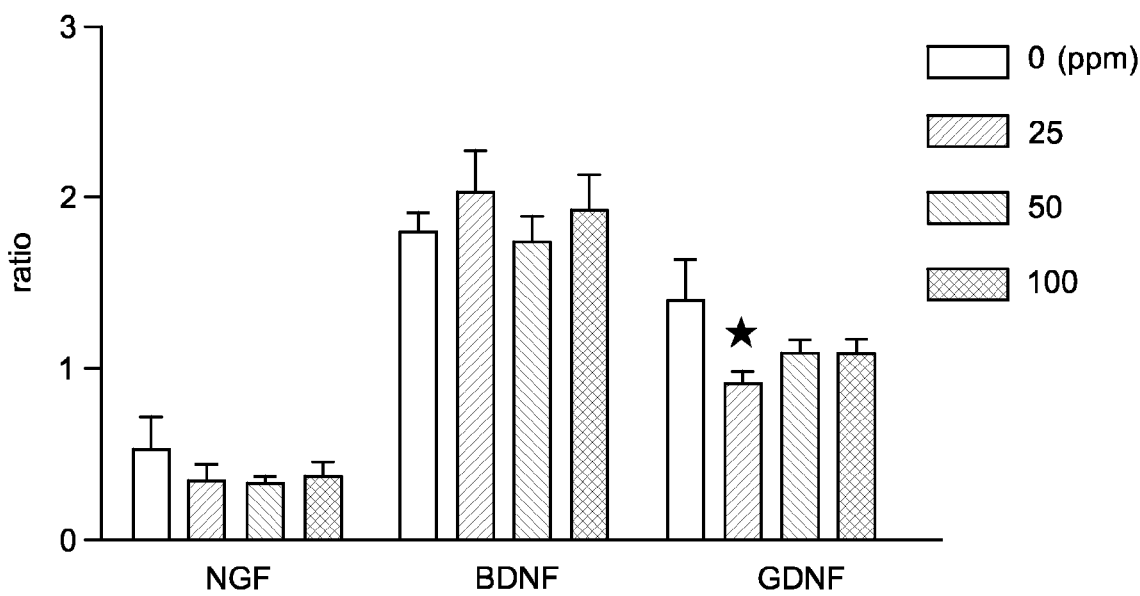
FIG. 3D—gene expression in NSC.

Results from the semiquantitative analysis of neurotrophic gene expression for C6 and NSC cultured on various chi-Au substrates are summarized in FIGS. 3C and 3D. The effects of gold on gene expression of C6 and NSC were different. In general, higher levels of both BDNF and GDNF genes were expressed than the NGF gene expression. Comparing chi-Au of different gold concentrations, higher NGF expression in C6 was detected at 50 ppm of gold, whereas the amount of BDNF and GDNF increased with the concentration of gold (FIG. 3C). On the contrary, there was no significant concentration dependence in the gene expression of NGF, BDNF, and GDNF in the NSC (FIG. 3D). For NGF and GDNF, the gene expression on chitosan alone was slightly higher than that at other concentrations; but the difference did not reach significance. For BDNF, the gene expression on chi-Au of all concentrations was similar. The only significance was that the GDNF gene expression at 25 ppm of gold was lower than that on chitosan alone.

The growth and orientation of NSC on the micropatterned surface were influenced by the 3-dimensional topography of the substrate. Most of the NSC appeared multipolar on the nonpatterned substrates and bipolar on the microgrooved substrates. The NSC on the nonpatterned surfaces did not exhibit a particular bias in alignment, but extended processes in a radial fashion. However, the morphology of NSC on the micropatterned surfaces had elongated processes oriented parallel to the grooves of the patterned substrate.

Figure 4:
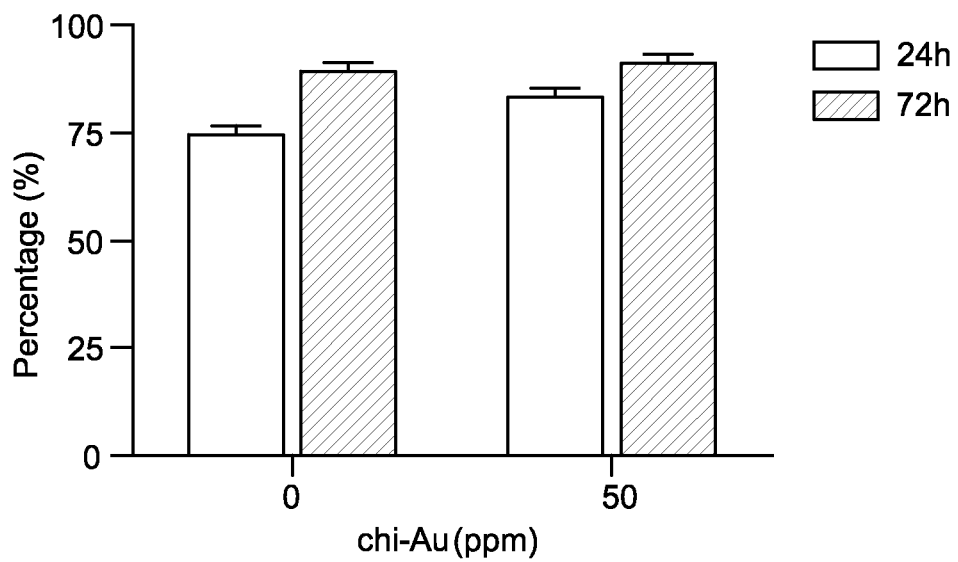
FIG. 4 shows the NSC alignment (percentage of cells aligned) at 24 and 72 hours.

The degree of cell orientation on the micropatterned substrates after 24 and 72 hours of culturing is shown in FIG. 4. The results show that, after 24 hours, 78.3% of the NSC were aligned on the chitosan substrate and 83.7% of the NSC were aligned on the chi-Au substrate. After 72 hours in culture, over 90% of cells were aligned in both substrates; and the alignment on chi-Au substrate was slightly better than on chitosan alone (not significant).

The SEM observations clearly showed that the microgrooves on the lumen surface of the conduits remained visible after the rolling procedure. The featured dimensions were also well kept.

The SFI values are listed in Table 5. The values at 3 weeks after operation were similar in both chi-Au groups with or without NSC. At the sixth week, the values were significantly greater than those at the third week for both groups. Especially, the SFI value in the NSC-seeded conduits was significantly greater than the value in the nonseeded chi-Au conduits.

TABLE 5

The Sciatic function index of the 2 experimental groups

| | Chi-Au | Chi-Au + NSC |
|---|---|---|
| At 3 wk | −72.62 ± 2.79 | −69.32 ± 4.16 |
| At 6 wk | −63.39 ± 10.10* | −48.74 ± 12.80*** |

The values represent means ± standard deviations.
*Significantly (P < 0.05) greater than at 3 weeks.
**Significantly (P < 0.05) greater than chi-Au.

No animals died after 6 weeks of implantation process. Macroscopically, the implant appeared as a discreetly enlarged area integrated in the sciatic nerve. The conduit was not yet degraded. The nerve was successfully connected; a white tubular substance through the conduit was observed. The histologic sections showed that the number of myelinated axons and the regenerated area were significantly greater in the NSC-preseeded conduit than in the conduit alone (Table 6). Angiogenesis was remarkable around the nerve fibers in the NSC-preseeded conduit.

TABLE 6

Data of histologic analyses at the midconduit from the 2 experimental groups

| | Chi-Au | Chi-Au + NSC |
|---|---|---|
| Regenerated area (mm²) | 0.298 ± 0.148 | 1.030 ± 0.424* |
| No. of myelinated axons | 453 ± 29 | 1938 ± 287* |
| No. of blood vessels | 18 ± 5 | 55 ± 11* |

The values represent means ± standard deviations.
*Significantly (P < 0.05) greater than chi-Au.

EXAMPLE 3

Effect of Chi-Ag on Cell Proliferation

Figure 5:
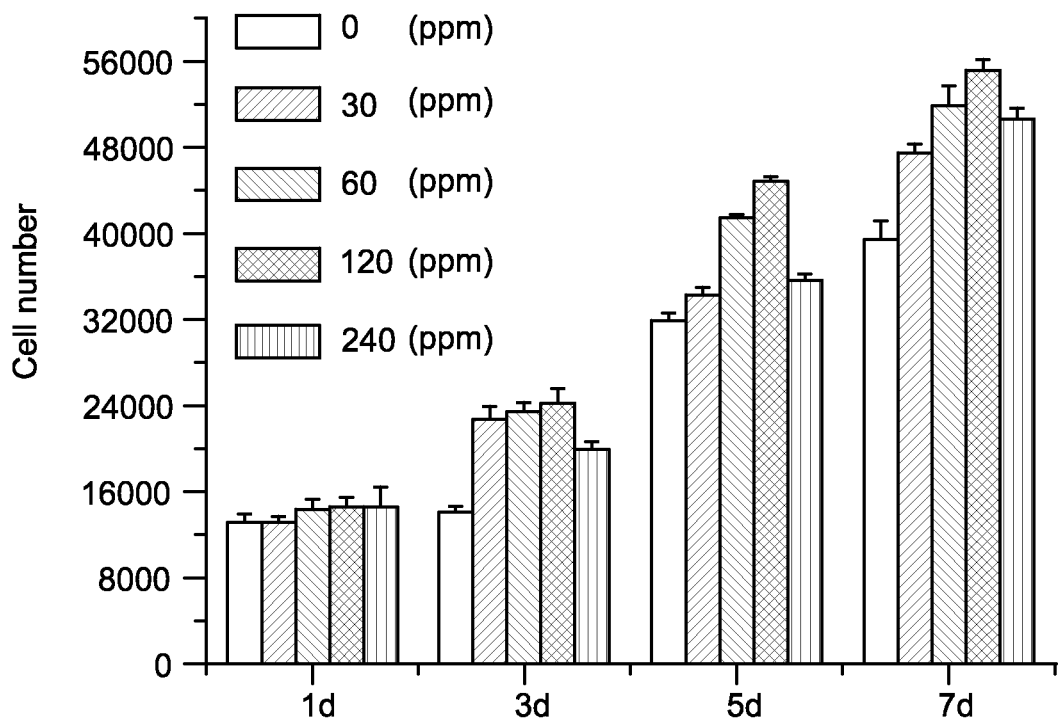
FIG. 5 shows the effect of chi-Ag on proliferation of cells.

In order to examine the applicability of other metals, chi-Ag nanocomposite was made and tested, and the result may be seen from FIG. 5. As shown, on day 3, the number of cells grown on material comprising chitosan and silver particles (5 nm) was 30 percent more than that of cells grown on material comprising chitosan. The effective concentration of the 5-nm silver particles was about 30 ppm over chitosan; however, it is believed that any concentration less than 500 ppm will be suitable, depending on the size of the particles. When particles with an average size of 25 nm or 50 nm were used, it was observed that the effective concentration of 60 ppm would be needed to increase the cell number up to 30 percent on day 3. Thus, a correlation between the size of particles and concentration may be inferred.

While certain embodiments have been described above, it will be understood that the embodiments described are by way of example only. Accordingly, the descriptions herein should not be limited based on the described embodiments. Rather, the descriptions herein should only be limited in light of the claims that follow when taken in conjunction with the above description and accompanying drawings

What is claimed is:

1. An implantable nerve regeneration device comprising,
    a micro-patterned conduit comprising a biodegradable polymer and a biocompatible metal; and
    a nerve regeneration enhancing element.

2. The device as claimed in claim 1, wherein the polymer comprises polyglucosamine.

3. The device as claimed in claim 1, wherein the polymer comprises chitosan.

4. The device as claimed in claim 1, wherein the polymer comprises polylactide.

5. The device as claimed in claim 1, wherein the concentration of the biocompatible metal over the polymer is less than 500 ppm.

6. The device as claimed in claim 1, wherein the concentration of the biocompatible metal over the polymer is between about 25 ppm and about 100 ppm.

7. The device as claimed in claim 1, wherein the nerve regeneration enhancing element comprises Schwann cells.

8. The device as claimed in claim 1, wherein the nerve regeneration enhancing element comprises neural stem cells.

9. The device as claimed in claim 8, wherein the neural stem cells comprise in their genome F1B-GFP gene.

10. The device as claimed in claim 1, wherein the nerve regeneration enhancing element comprises a growth factor.

11. The device as claimed in claim 1, wherein the nerve regeneration enhancing element comprises fibroblast growth factor 1.

12. The device as claimed in claim 1, wherein the micro-patterned conduit has an inner surface on which a microgroove is formed, the microgroove having a dimension capable of accommodating the nerve regeneration enhancing element.

13. The device as claimed in claim 1, wherein the micro-patterned conduit has an inner surface on which a microgroove is formed, the microgroove having a width between about 1 to about 50 micrometer, a spacing between about 1 to about 50 micrometer, and a depth between about 0.1 to about 15 micrometer.

* * * * *